US010085870B2

(12) United States Patent
Pflaster et al.

(10) Patent No.: US 10,085,870 B2
(45) Date of Patent: Oct. 2, 2018

(54) JOINT BRACE WITH IMPROVED RANGE OF MOTION STOP

(71) Applicant: Horsepower Technologies Inc., Lowell, MA (US)

(72) Inventors: Daniel Scott Pflaster, Charlotte, VT (US); Wendy Drumm, Providence, RI (US); Richard L. Miller, Needham, MA (US); Kristin Jugenheimer Size, Waltham, MA (US); Gregory Scott Torrisi, Midlothian, VA (US)

(73) Assignee: HORSEPOWER TECHNOLOGIES INC., Lowell, MA (US)

( * ) Notice: Subject to any disclaimer, the term of this patent is extended or adjusted under 35 U.S.C. 154(b) by 481 days.

(21) Appl. No.: 14/545,799

(22) Filed: Jun. 22, 2015

(65) Prior Publication Data
US 2016/0367392 A1    Dec. 22, 2016

(51) Int. Cl.
A61F 5/01    (2006.01)

(52) U.S. Cl.
CPC .............. A61F 5/0127 (2013.01); A61F 5/01 (2013.01); A61F 5/013 (2013.01); A61F 5/0195 (2013.01); A61F 2005/0137 (2013.01); A61F 2005/0139 (2013.01); A61F 2005/0165 (2013.01); A61F 2005/0167 (2013.01); A61F 2005/0179 (2013.01)

(58) Field of Classification Search
CPC .......... A61F 5/0127; A61F 5/01; A61F 5/013; A61F 5/0195; A61F 5/0102; A61F 5/0123; A61F 5/0125; A61F 2005/0137; A61F 2005/0139; A61F 2005/0148; A61F 2005/0155; A61F 2005/0158; A61F 2005/0165; A61F 2005/0167; A61F 2005/0179; A61D 9/00; Y10T 403/32591; Y10T 403/32549; Y10T 403/32254; Y10T 403/32557; E05B 17/0012; E05B 17/0037; E05B 17/042; E05B 37/0058; E05B 47/0003; E05B 47/0004; E05B 2047/002; E05B 2047/0021; E05B 55/00; E05B 55/06; E05B 69/00; E05B 79/08; E05B 79/10; E05B 63/0017; E05B 13/101; E05C 1/08; E05C 1/085; E05C 3/12; E05C 3/124; E05C 9/02; E05C 19/16; E05C 19/165; A01K 13/006; A01K 13/007
See application file for complete search history.

(56) References Cited

U.S. PATENT DOCUMENTS

| | | |
|---|---|---|
| 121,880 A | 12/1871 | Lewis |
| 901,592 A | 10/1908 | Clegg |
| 2,512,925 A | 6/1950 | Eggeman |
| 2,937,487 A | 5/1960 | Dever |
| 3,193,984 A | 7/1965 | Schubert |
| 3,209,517 A | 10/1965 | Hyman |
| 3,439,670 A | 4/1969 | Schuerch |

(Continued)

Primary Examiner — Alireza Nia
Assistant Examiner — Rachel Berezik
(74) Attorney, Agent, or Firm — Foley & Lardner LLP

(57) ABSTRACT

An improved joint support for limiting the range of motion of an anatomical joint comprises intermeshing gears for allowing adjustment of the range of motion of the joint, and comprises plural mechanisms for securing the gears in engagement with one another, whereby adjustment can be made without tools and without disassembly of any components.

20 Claims, 12 Drawing Sheets

(56) References Cited

U.S. PATENT DOCUMENTS

| | | | |
|---|---|---|---|
| 4,099,269 A | 7/1978 | Porner | |
| 4,370,977 A | 2/1983 | Mauldin | |
| 4,471,538 A | 9/1984 | Pomeranz | |
| 4,538,602 A | 9/1985 | Shapiro | |
| 4,961,416 A | 10/1990 | Moore | |
| 5,107,827 A | 4/1992 | Boyd | |
| 5,115,627 A | 5/1992 | Scott | |
| 5,152,285 A | 10/1992 | Gnegy | |
| 5,201,776 A | 4/1993 | Freeman | |
| 5,363,632 A | 11/1994 | Amato | |
| 5,376,066 A | 12/1994 | Phillips et al. | |
| 5,437,619 A * | 8/1995 | Malewicz | A61F 5/0125 602/16 |
| 5,441,015 A | 8/1995 | Farley | |
| 5,545,128 A | 8/1996 | Hayes et al. | |
| 5,579,627 A | 12/1996 | Vogt | |
| 5,599,290 A | 2/1997 | Hayes et al. | |
| 5,658,241 A | 8/1997 | Deharde | |
| 5,662,594 A | 9/1997 | Rosenblatt | |
| 5,672,152 A | 9/1997 | Mason | |
| 5,794,261 A | 8/1998 | Hefling | |
| 5,816,032 A | 10/1998 | Vogt | |
| 5,827,208 A * | 10/1998 | Mason | A61F 5/0125 602/16 |
| 5,861,175 A | 1/1999 | Walters et al. | |
| 5,871,458 A | 2/1999 | Deny | |
| 5,910,126 A | 6/1999 | Wilson et al. | |
| 6,033,373 A | 3/2000 | Davis | |
| 6,039,709 A | 3/2000 | Bzoch | |
| 6,117,097 A | 9/2000 | Ruiz | |
| 6,151,873 A | 11/2000 | Rogers | |
| 6,368,613 B1 | 4/2002 | Walters et al. | |
| 6,387,066 B1 | 5/2002 | Whiteside | |
| 6,553,994 B2 | 4/2003 | Bard | |
| 6,883,466 B1 | 4/2005 | Chambers | |
| 6,918,236 B2 | 7/2005 | Springs | |
| 7,402,147 B1 | 7/2008 | Allen | |
| 7,559,910 B2 | 6/2009 | Daly | |
| 7,608,314 B2 | 10/2009 | Plant | |
| 7,789,844 B1 | 9/2010 | Allen | |
| 7,837,640 B2 | 11/2010 | Greenwald et al. | |
| 7,896,019 B2 | 3/2011 | Bettin et al. | |
| 8,894,594 B2 | 11/2014 | Pflaster et al. | |
| 9,044,306 B2 | 6/2015 | Pflaster et al. | |
| 2002/0077368 A1 | 6/2002 | Walters et al. | |
| 2003/0153853 A1 | 8/2003 | Houser | |
| 2003/0199798 A1 * | 10/2003 | Gilmour | A61F 5/0127 602/16 |
| 2004/0055543 A1 | 5/2004 | Clement | |
| 2004/0153016 A1 * | 8/2004 | Salmon | A61F 5/0125 602/16 |
| 2004/0255955 A1 | 12/2004 | Daly | |
| 2005/0059908 A1 | 3/2005 | Bogert | |
| 2005/0187505 A1 | 8/2005 | Carlson | |
| 2005/0215931 A1 * | 9/2005 | Opahle | A61F 5/0125 602/23 |
| 2006/0107909 A1 | 5/2006 | White | |
| 2006/0155230 A1 | 7/2006 | Mason | |
| 2006/0231045 A1 | 10/2006 | Lindley | |
| 2008/0200856 A1 | 8/2008 | Cadichon | |
| 2009/0094949 A1 | 4/2009 | Heid et al. | |
| 2009/0137935 A1 | 5/2009 | Nace | |
| 2009/0288377 A1 | 11/2009 | Heid et al. | |
| 2010/0056973 A1 | 3/2010 | Farrow et al. | |
| 2010/0100021 A1 | 4/2010 | Einarsson | |
| 2010/0132099 A1 | 6/2010 | Green et al. | |
| 2010/0192290 A1 | 8/2010 | Husain | |
| 2011/0009786 A1 * | 1/2011 | Chan | A61F 5/0125 602/16 |
| 2011/0034848 A1 | 2/2011 | Lutz | |
| 2012/0041348 A1 * | 2/2012 | Maekita | A61F 5/0102 601/34 |
| 2013/0253393 A1 * | 9/2013 | Schilling | A61F 5/0102 602/5 |
| 2013/0338555 A1 | 12/2013 | Pflaster et al. | |
| 2014/0148746 A1 * | 5/2014 | Pflaster | A61D 9/00 602/16 |
| 2015/0051528 A1 * | 2/2015 | Gilbert | A61F 5/01 602/16 |
| 2015/0141888 A1 * | 5/2015 | Chiang | A61F 5/0125 602/16 |

* cited by examiner

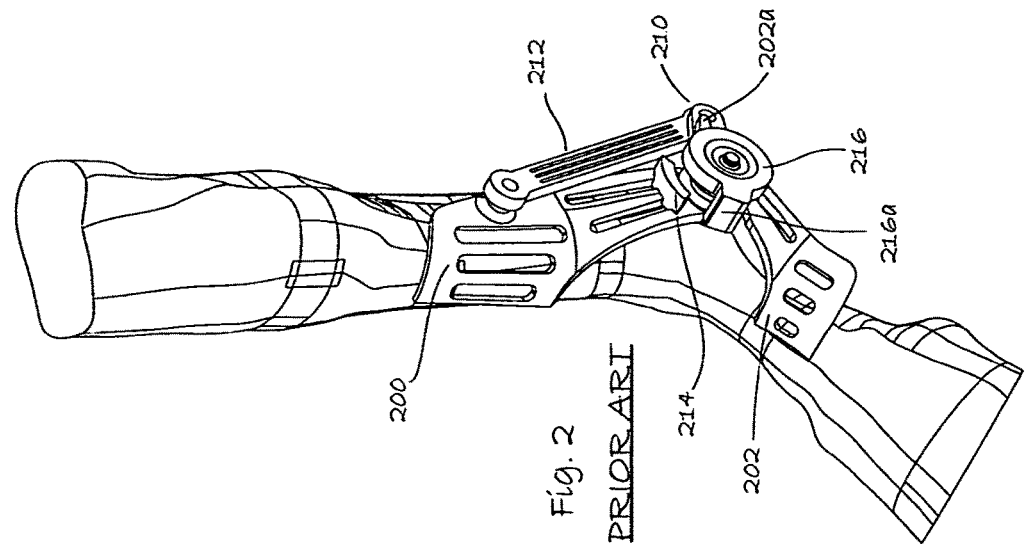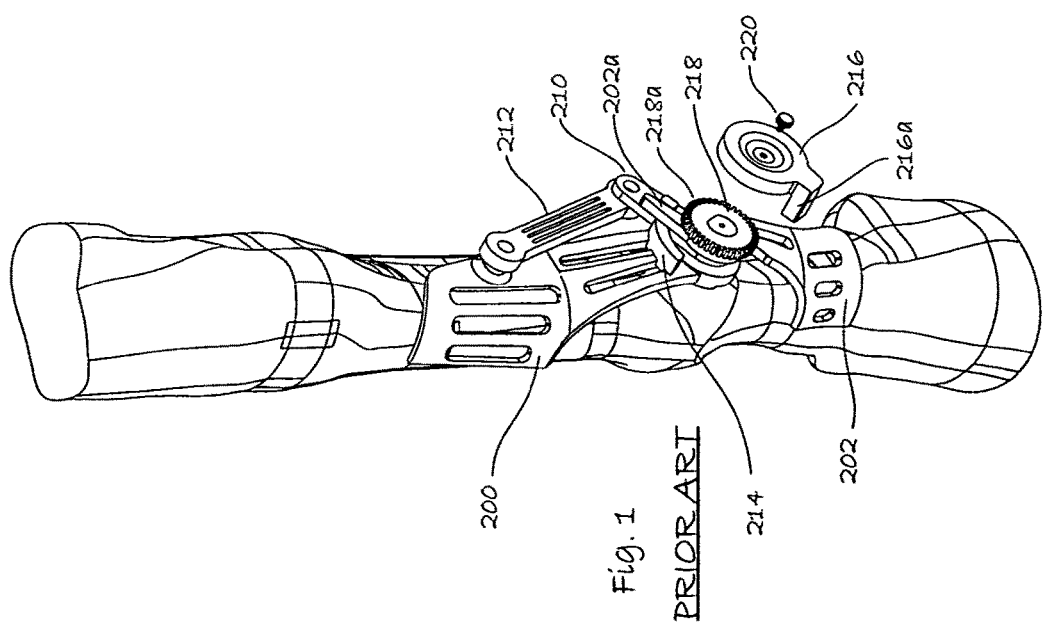

SECTION B-B

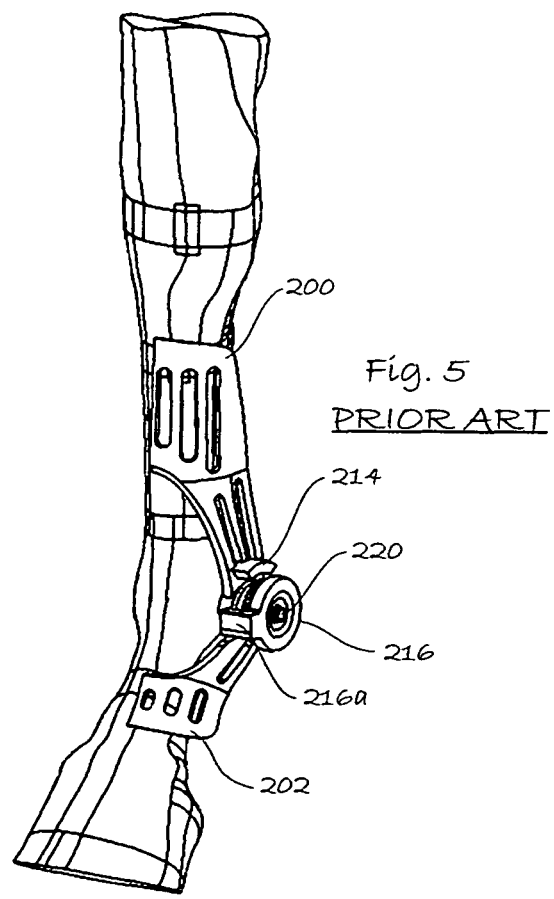

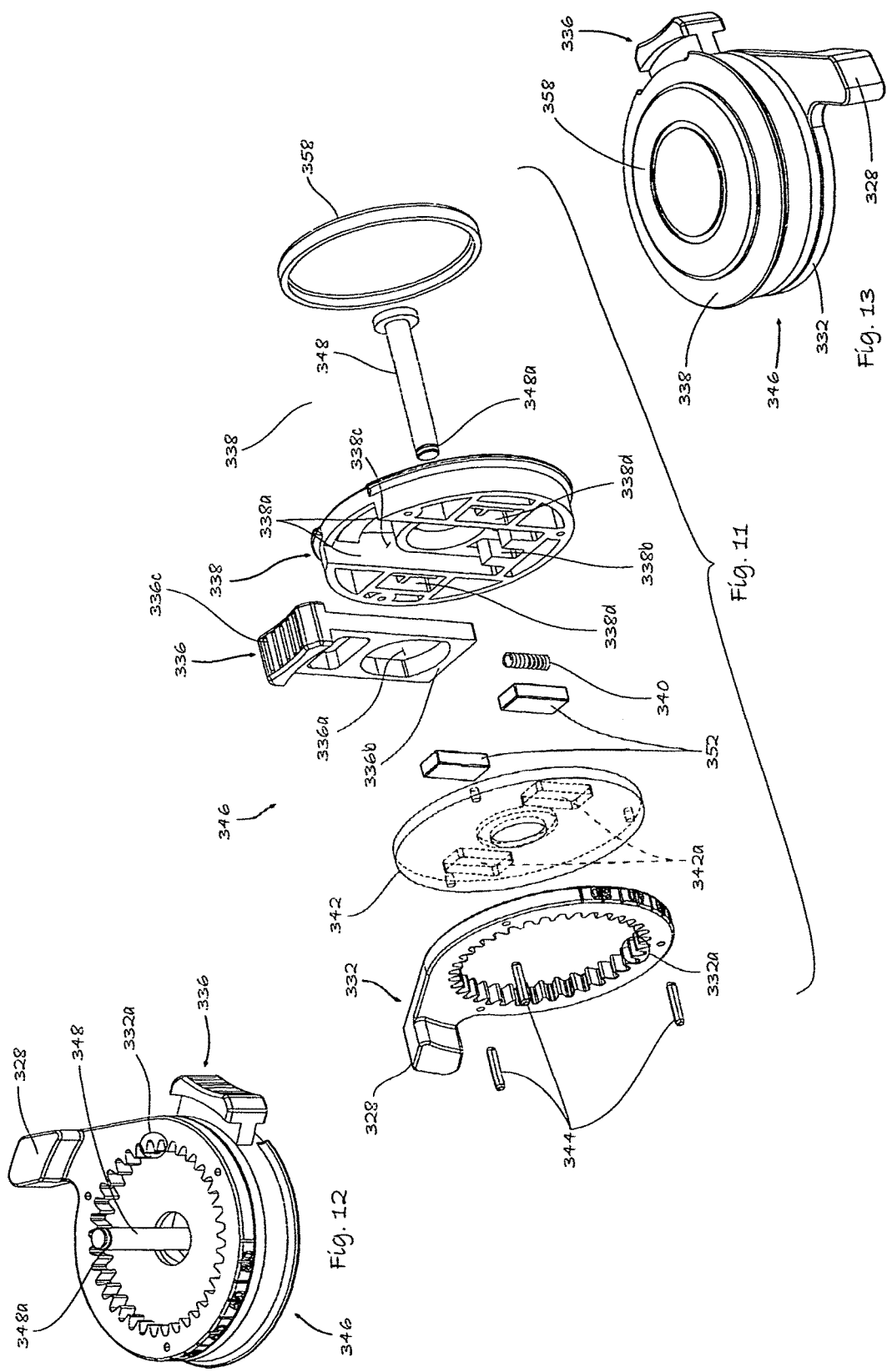

JOINT BRACE WITH IMPROVED RANGE OF MOTION STOP

FIELD OF THE INVENTION

This invention relates to an improved joint brace for an anatomical joint, such as the fetlock of a horse, which is provided with convenient and reliable adjustment for the range of motion (ROM) permitted to the joint. This is useful during training, for rehabilitation after injury or surgery, and otherwise.

BACKGROUND OF THE INVENTION

The present inventors and others have filed several generally relevant prior applications, including Ser. No. 61/321,212, filed Apr. 6, 2012, Ser. No. 13/064,644, filed Apr. 5, 2011, now U.S. Pat. No. 8,894,594, Ser. No. 13/694,621, filed Dec. 18, 2012, now U.S. Pat. No. 9,044,306, and Ser. No. 14/106,300, filed Dec. 13, 2013. Priority from these prior applications is not being claimed at the initial filing of this application, although applicant reserves the right to later claim priority therefrom if deemed necessary.

Of the above, Ser. No. 14/106,300 is the most recent, and the most relevant to the present invention. Ser. No. 14/106,300 discloses a joint brace with an adjustable ROM stop, as does this application. The adjustable ROM stop of the present invention, and the joint brace employing it, are novel and unobvious over that shown by Ser. No. 14/106,300.

More specifically, FIGS. 33-36 of Ser. No. 14/106,300 disclose a joint brace, optimized to support the fetlock of a horse, incorporating a ROM stop as well as resilient members adapted to add to the ability of the horse's joint structure to support it as the joint moves in extension. FIG. 37 discloses the ROM stop without the resilient members. The ROM stop of the present invention is likewise useful in connection with joint braces both with and without resilient members.

For convenience, FIGS. 33-37 of Ser. No. 14/106,300 (published as application 2014/0148746) are reproduced in this application as FIGS. 1-5, respectively. The text describing these is reproduced below, with the figure numbers corrected accordingly, as follows:

"FIGS. 1-3 show a further refinement, employing the same structure as explained above with respect to FIGS. 31 and 32, but incorporating as well a range of motion (ROM) stop. Limiting the range of motion of the joint can be helpful in rehabilitation of musculoskeletal structures—again, both hard and soft tissues—after injury or surgery. Early return to function is pivotal to the patient's successful recovery from injury. Some early range of motion exercises help attenuate adhesive scar tissue formation, promote more normal tissue formation, and thereby increase functionality. Muscle atrophy is also less than would occur if the lower limb was completely immobilized. However, unrestricted exercise is counterproductive, setting the stage for reinjury or new lesion formation and a more prolonged and possibly unsuccessful outcome. Adjustment of the ROM to optimize it to the patient's specific recovery status is desirable; generally, as the patient recovers, the ROM can be gradually increased.

"This is accomplished in the embodiment shown by providing a ROM stop member 216, held to pin 204 (FIG. 4) by a screw 220. As shown by the exploded view of FIG. 1, a gear wheel 218 having external teeth 218a is keyed to the lower cuff 202. The ROM stop member 216 has internal gear teeth (not shown) which mate with the external teeth of gear wheel 218. The mating internal and external peripheral teeth shown could be replaced with radial teeth on the mating faces of the ROM stop member 216 and the lower cuff 202. ROM stop member 216 also comprises an arm 216a, which is arranged to bear against stop 214 on the upper cuff 200. Thus, as the joint is extended, ROM stop member 216 rotates along with lower cuff 202 until arm 216a contacts stop 214, limiting the ROM of the joint. As the patient recovers, and increased ROM becomes desirable, the relative position of ROM stop member 216 with respect to lower cuff 202 can be adjusted simply by removing screw 220, removing ROM stop member 216 sufficiently to disengage the teeth from one another, turning it counterclockwise and replacing it in its new position.

"There are numerous alternative designs for the ROM stop that will occur to those of skill in the art, and are to be considered within the scope of the invention. These include a non-extensible cord, extending between the fixing points of the resilient tension member 212, and of length appropriate to limit the ROM as desired. Adjustment of ROM could be provided by use of cords of different lengths, or providing a choice of fixing points that would provide differing effective lengths. The cord could also be provided in the form of a tubular length of webbing, possibly encasing the resilient tension member 212. Other alternatives include a plate affixed to the upper cuff 200 in the approximate position of stop 214, with a number of holes for receiving a stop pin that would bear against a block on lower cuff 202; by provision of a number of holes for the stop pin, the ROM could be adjusted.

"It is also desirable to provide adjustment of the tension exerted by the resilient tension member 212; for example, as the joint recovers from injury or surgery, it may be desirable to gradually reduce the tension exerted for a given degree of joint flexion. This can be accomplished in a variety of ways. For example, one or more of the flat ribbons 212c of the resilient tension member 212 can simply be cut away. Different resilient tension members 212 having different characteristics can be employed, or multiple resilient tension members 212 can be employed initially, and be removed progressively as the joint recovers. The attachment point of the resilient tension member 212 on either upper cuff 200 or on wing member 210 can be varied, as can the design of the wing member 210; if the wing member 210 is effectively lengthened, e.g., by proving multiple attachment points along its length, more tension will be exerted for a given degree of joint extension. Likewise, the point at which the resilient tension member 212 begins to exert tension and support the joint can be varied as desired by variation of the geometry of the device.

"It will also be appreciated by those of skill in the art that the function of resilient tension member 212 could be provided by other types of devices, such as tension, compression, leaf, hairpin or torsion springs. The cord containing a dilatant material discussed above with respect to FIG. 16 could also be employed. These are to be considered within the meaning of "resilient tension member" except where the context or explicit language excludes such alternative devices.

"It is also within the scope of the invention that the device could also be made such that the resilient tension members on either side of the brace could be adjusted independently of one another. For example, it may be desirable to provide more tension on one side than the other when the injury is asymmetric.

"As noted, the embodiment of FIGS. 31 and 32 includes the resilient tension member for assistance in bearing the tensile loads on the tendons, while the embodiments of FIGS. 1-3 add to this the ROM stop feature. It is also within the scope of the invention to provide the ROM stop feature without the resilient tension member; this could also be useful in rehabilitation. FIG. 5 shows modification of the device shown to include the ROM stop only. As illustrated, again a ROM stop member 216 is secured to the lower cuff by an arrangement allowing adjustment of their relative radial positions. ROM stop member 216 comprises an arm 216a arranged to bear against a stop 214 secured to the upper cuff 200."

Thus, as indicated above, Ser. No. 14/106,300 discloses a joint support incorporating a ROM stop. The present application does so as well, but incorporates further improvements in the ROM stop.

SUMMARY OF THE INVENTION

The specific improvements made by the present invention relate to adjustment of the ROM permitted. In the embodiment disclosed by Ser. No. 14/106,300, the adjustment is made by removing a small screw 220, freeing ROM stop member 216, pulling ROM stop member 216 axially outwardly sufficiently to disengage internal gear teeth formed on the inside of ROM stop member 216 from external teeth of gear wheel 218, turning the ROM stop member 216 in the desired direction (counterclockwise in order to increase ROM, in the FIG. 1 view) replacing it in its new position, and securing it with screw 220.

It will be apparent that this procedure requires a screwdriver or other tool, and that in the typical barnyard or horse stall it would be easy to lose the screw 220, particularly if the horse should move while one is attempting to reinsert the screw 220. Even if the screw were replaced by another fastener that could be operated by hand, such as a thumbscrew, the screw could nonetheless come loose during exercise, allowing the ROM stop assembly to fall off, which could lead to overextension of the joint and possible injury. It is therefore an object of the invention to provide a ROM stop that can be adjusted without tools, and without any components becoming detached.

According to the invention, the cooperating gears which determine the ROM are secured in their operative position by a sliding latch locking structure, operable by hand, so as to eliminate the possibility of the removable portion of the assembly becoming accidentally detached. One or more magnets retained in the assembly so as to avoid being lost may additionally be provided; these require application of force to "unlock" the ROM adjuster, reducing the possibility of the device's coming loose during exercise.

Another object of the invention is to provide a directly-readable scale indicating the ROM permitted, so as to simplify adjustment. This is accomplished according to the invention by provision of cooperating indicia around the periphery of the adjustable portion of the assembly.

BRIEF DESCRIPTION OF THE DRAWINGS

The invention will be better understood if reference is made to the accompanying drawings, in which:

FIG. 1, corresponding to FIG. 33 of Ser. No. 14/106,300, shows a perspective view of the prior art joint support, showing the ROM stop in partially exploded view, with the joint straight;

FIG. 2, corresponding to FIG. 34 of Ser. No. 14/106,300, shows a view similar to FIG. 1, and of the same embodiment, with the joint extended;

FIG. 5, corresponding to FIG. 37 of Ser. No. 14/106,300, is a view similar to FIG. 1, illustrating a further modification;

FIG. 11 shows an enlarged exploded view of the ROM stop assembly, which, as will be discussed in detail below, is moved axially outwardly and rotated to adjust the ROM permitted;

FIG. 12 shows a perspective view of the ROM stop assembly, showing the interior thereof;

FIG. 13 shows a perspective view of the ROM stop assembly, showing the exterior thereof;

DETAILED DESCRIPTION OF THE PREFERRED EMBODIMENT

As indicated above, it is an object of the invention to provide a joint brace with an improved ROM stop mechanism permitting the ROM to be adjusted without tools, and without any disassembly, so that parts cannot be lost and the ROM can be adjusted conveniently. It is a further object of the invention to provide readily-visible indicia that describe the ROM provided, for convenience and consistency of the ROM setting.

These objects are met by the joint brace and improved ROM stop mechanism of the invention, as will appear below.

As in Ser. No. 14/106,300, the joint brace comprises upper and lower cuffs secured to the anatomical structure on either side of the joint to be protected, and pivoted to one another at medial and lateral pivot points so as to define a pivot axis approximately coinciding with the anatomical joint. Cooperating stop members secured to the upper and lower cuffs abut on extension of the joint to limit the ROM of the joint. The ROM is adjusted by adjustment of the point at which the cooperating members abut.

Also as in Ser. No. 14/106,300 a fixed stop is secured to one of the upper and lower cuffs, and an adjustable ROM stop to the other of the upper and lower cuffs. The adjustable ROM stop is provided on an outer gear with internal teeth, while an inner gear with external teeth is fixed to the other of the upper and lower cuffs. Adjustment of ROM is accomplished by moving the outer gear axially outwardly to disengage it from the fixed gear, permitting repositioning.

As will be apparent, for the joint brace to function properly to limit ROM, the components must be securely fastened to one another so as to not become disengaged in use. In Ser. No. 14/106,300 this was accomplished using a single screw. This allowed the possibility that the screw could come loose or be lost, and the screw might be difficult to reinsert under some circumstances.

According to the present invention, a mechanism is provided to secure the components of the brace in the desired position to control ROM, while permitting adjustment to be made without disassembly, and without tools. A first securing mechanism includes a hand-operable sliding latch mechanism that positively locks the components in the desired position, but can be readily released to allow adjustment of the ROM. A second securing mechanism employs magnets to secure the components of the ROM stop mechanism to one another.

In the following, we describe the joint brace comprising the improved ROM stop mechanism of the invention. Common components are commonly numbered, and the features of the invention most clearly illustrated by the various views will be described with respect to each.

Figure 8:
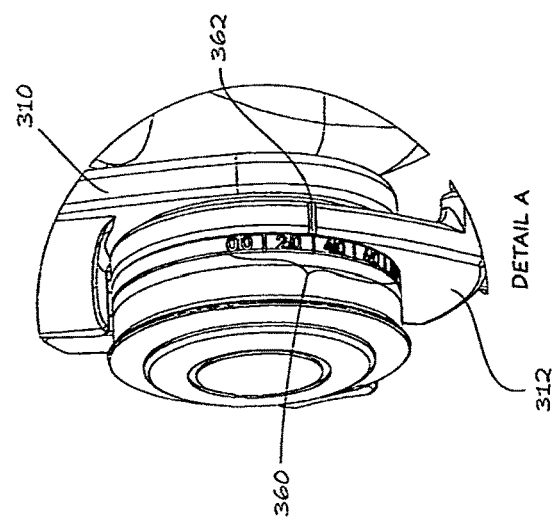
FIG. 8 shows an enlarged detail view taken at A in FIG. 7.
Figure 7:
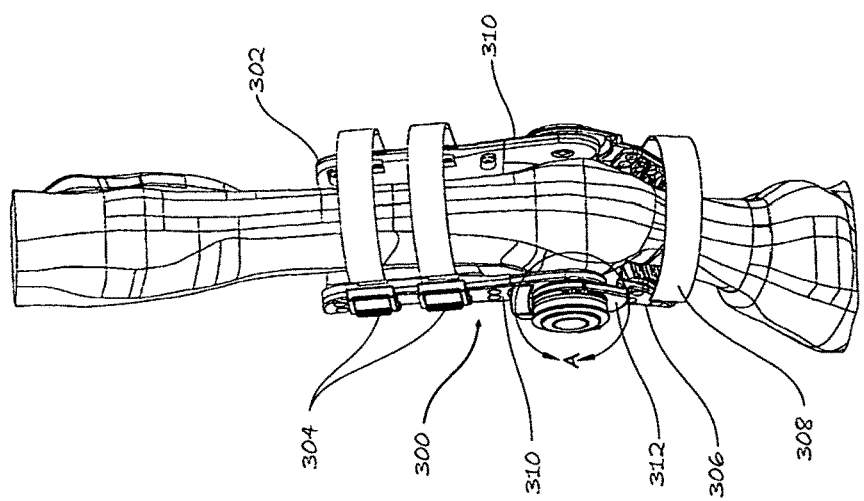
FIG. 7 shows a perspective rear view thereof.
Figure 6:
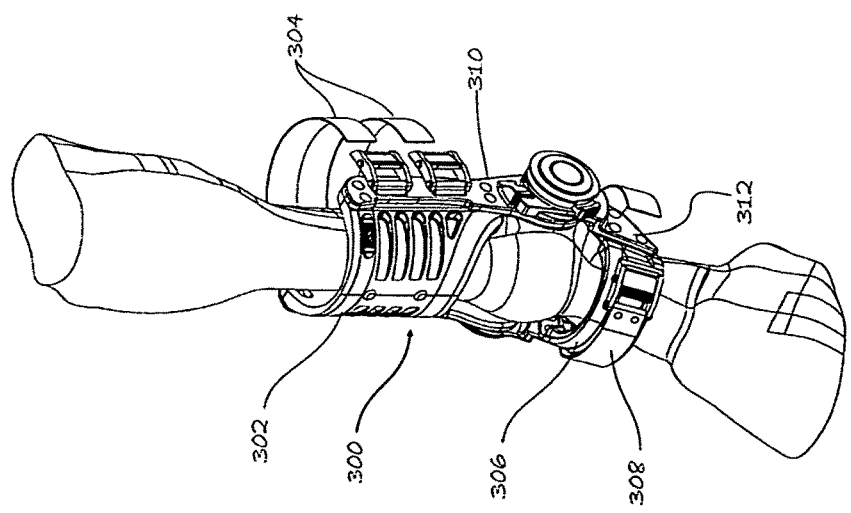
FIG. 6 shows a perspective front view of the joint brace of the invention, incorporating the improved ROM stop.
Figure 9:
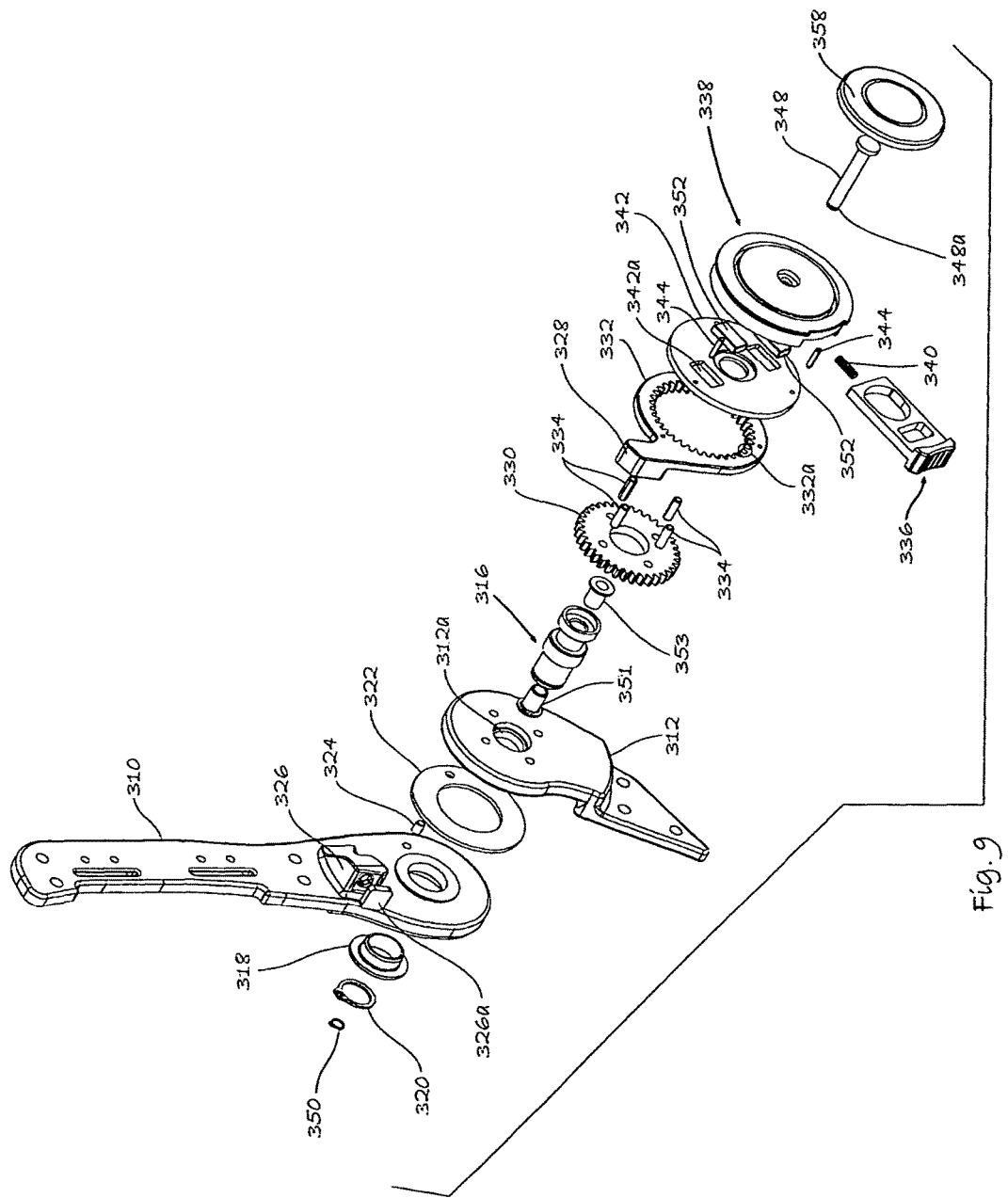
FIG. 9 shows an exploded view of the ROM stop of the invention, from the lateral side.
Figure 10:
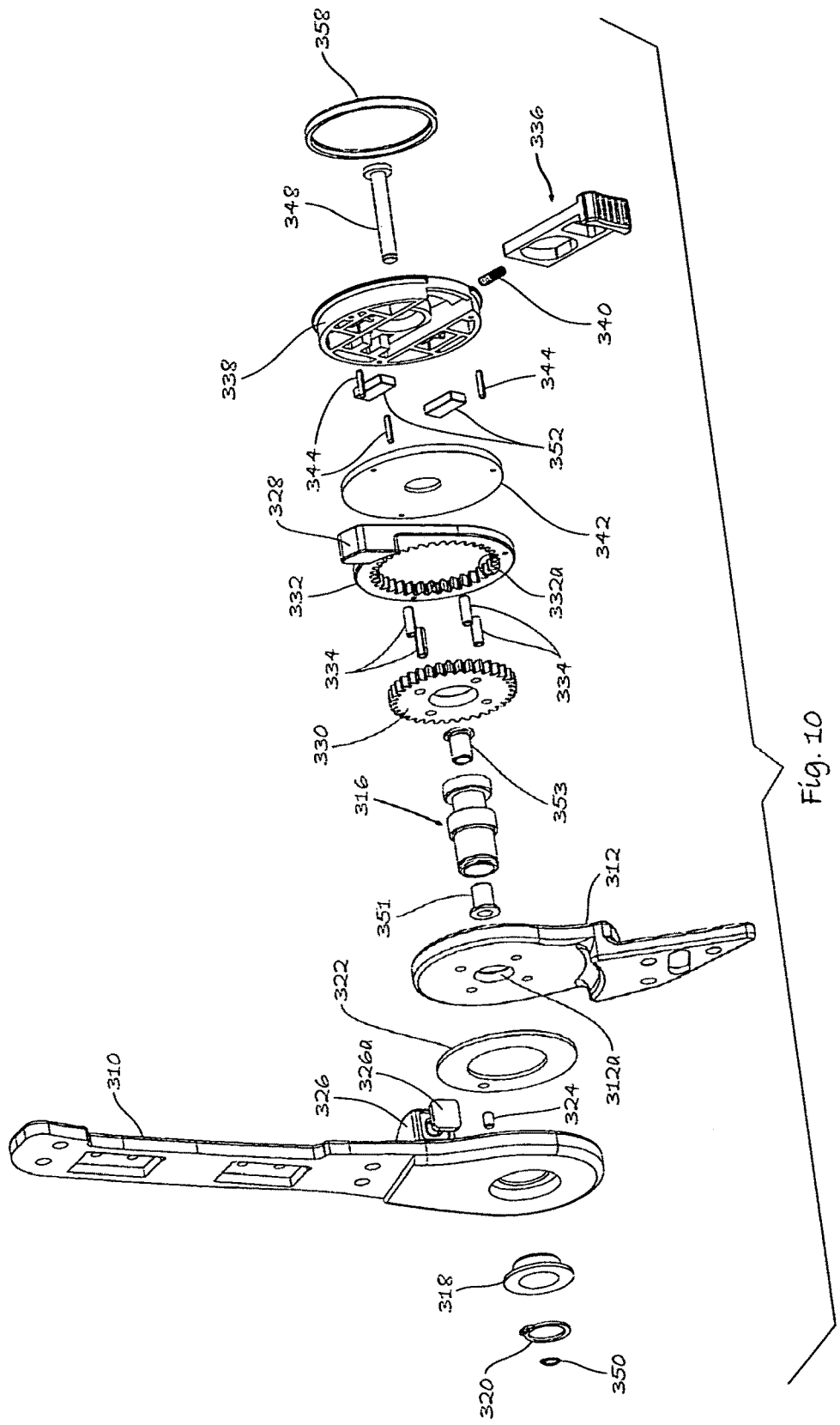
FIG. 10 shows an exploded view of the ROM stop of the invention, from the medial side.
Figure 14:
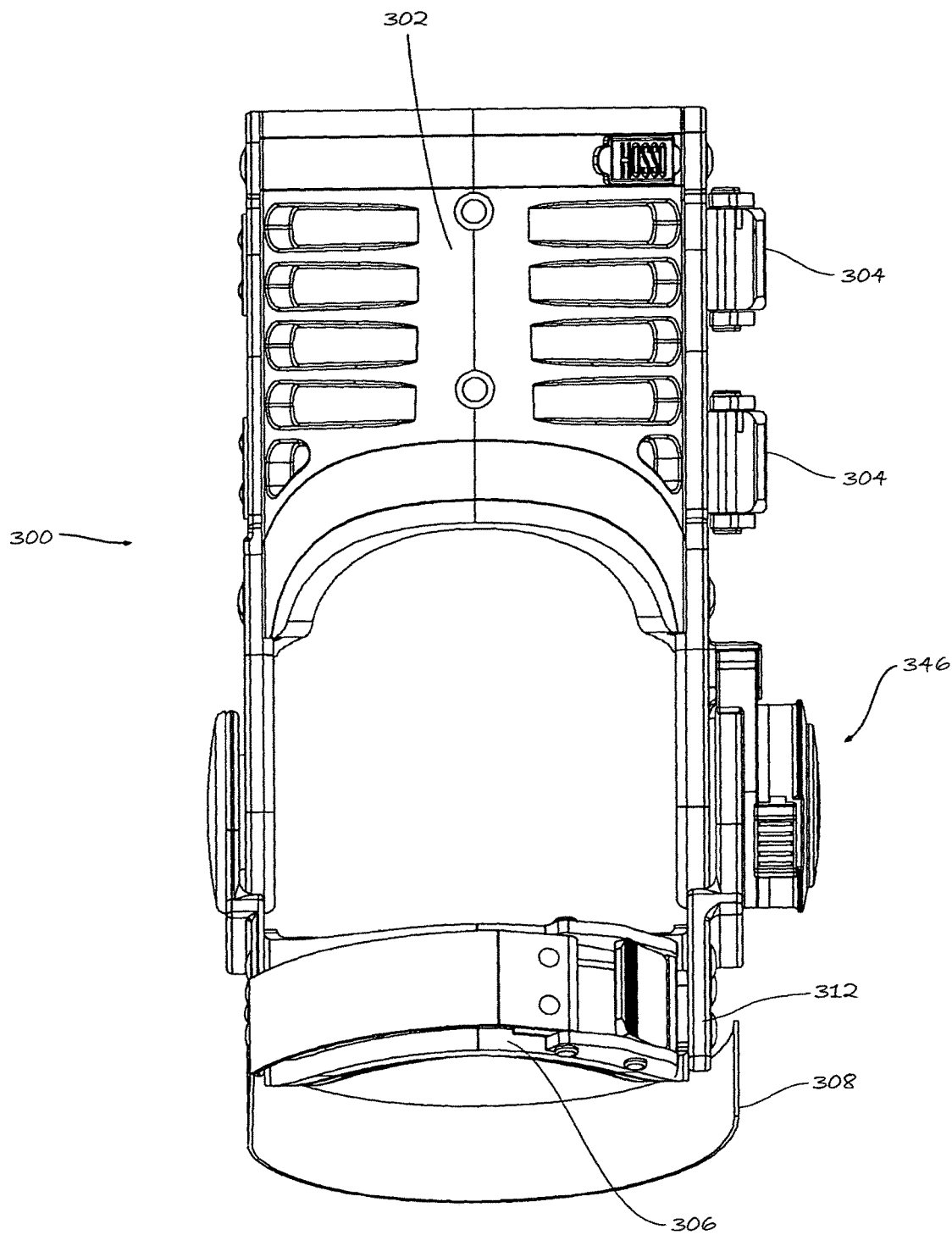
FIG. 14 shows an elevation of the joint brace of the invention.

Thus, FIGS. 6, 7, 14 and 16 show views of the complete joint brace, and FIG. 8 shows a detail of FIG. 7 at larger scale, for clarity. FIGS. 6 and 7 show the brace as employed to limit the ROM of a horse's fetlock, but it will be appreciated that the joint brace of the invention would be useful with other anatomical joints, including human.

The joint brace 300 comprises an upper proximal cuff 302 secured to an upper member of the joint the ROM of which is to be limited (in the case of a horse's fetlock, the cannon bone), by straps 304, and a lower distal cuff 306 secured to the other member of the joint (in the case of a horse's fetlock, the pastern bone), by a strap 308. Cuffs 302 and 306 may be molded of a tough plastic material or the like.

The upper and lower cuffs 302 and 306 respectively are joined to one another by way of upper proximal and lower distal side plates 310 and 312 respectively, which are provided on both medial and lateral sides of the joint brace 300. The ROM stop mechanism need only be provided on one side of the joint brace 300; as illustrated, it is typically employed only on the lateral side, so as to avoid interference with the horse's opposite leg.

Figure 15:
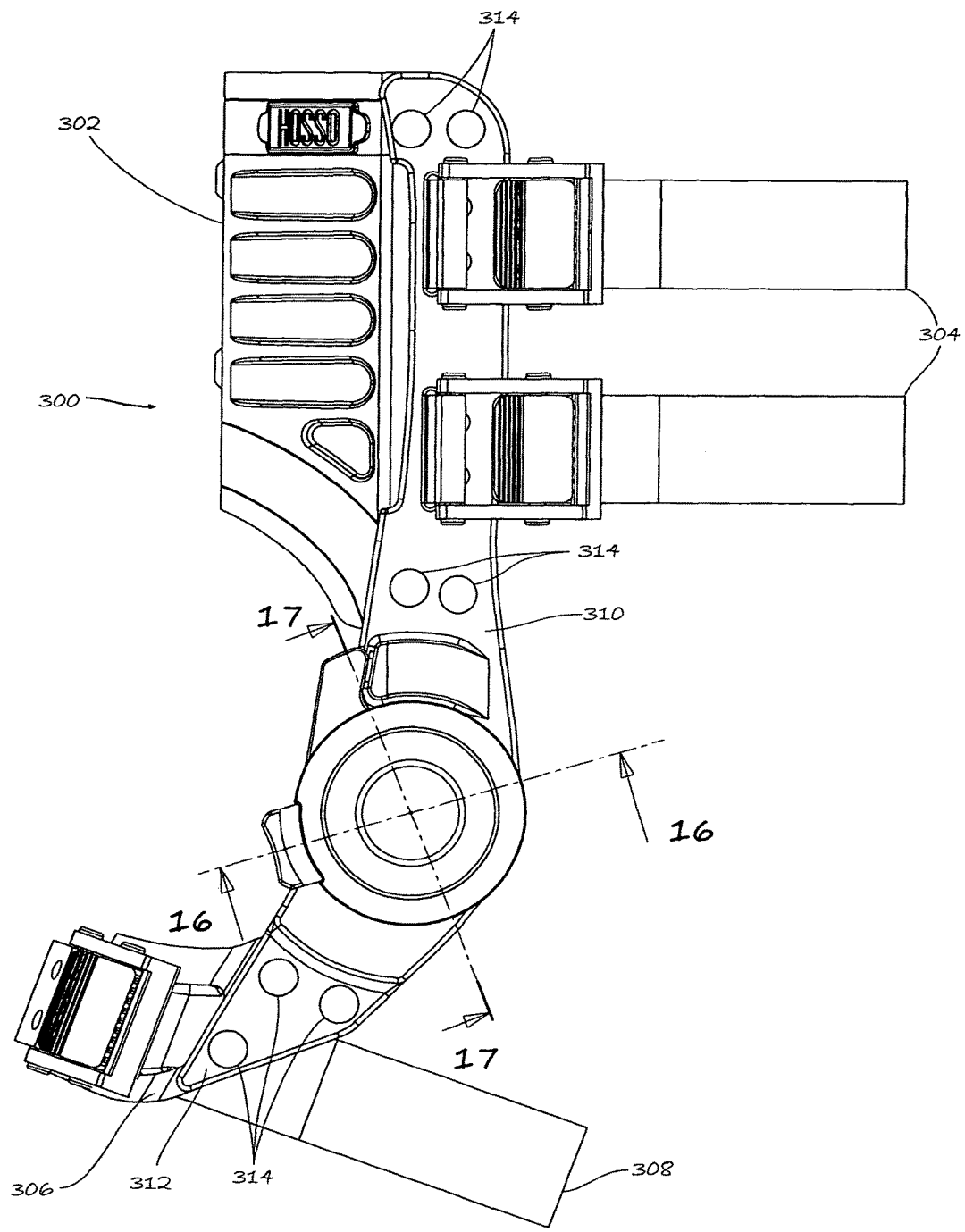
FIG. 15 is a side view of the joint brace of the invention.

The upper and lower cuffs 302 and 306 respectively are joined to the upper and lower side plates 310 and 312 respectively by rivets or other fasteners, as indicated at 314 (FIG. 15).

The upper and lower side plates 310 and 312 respectively are secured to one another so as to pivot freely about a pivot axis that is substantially aligned with the anatomical joint to be protected. The structure defining the lateral pivot axis between the upper and lower side plates 310 and 312 respectively is shown in detail, and forms a part of the ROM stop assembly, as will appear below; the medial pivot structure is generally similar.

The structure defining the lateral pivot axis between the upper and lower side plates 310 and 312 respectively comprises a central pivot axle 316. In the embodiment shown, pivot axle 316 is radially symmetric, so that it can be turned from a cylinder of metal or plastic (depending on the use; a joint brace for a horse's fetlock will likely need to be made of metal, while one for, for example, a human wrist could be made of plastic), or molded in a single piece. The detailed structure of pivot axle 316 is shown separately in FIGS. 18 and 19, so as to avoid cluttering the other drawings with excessive reference numerals.

Figure 19:
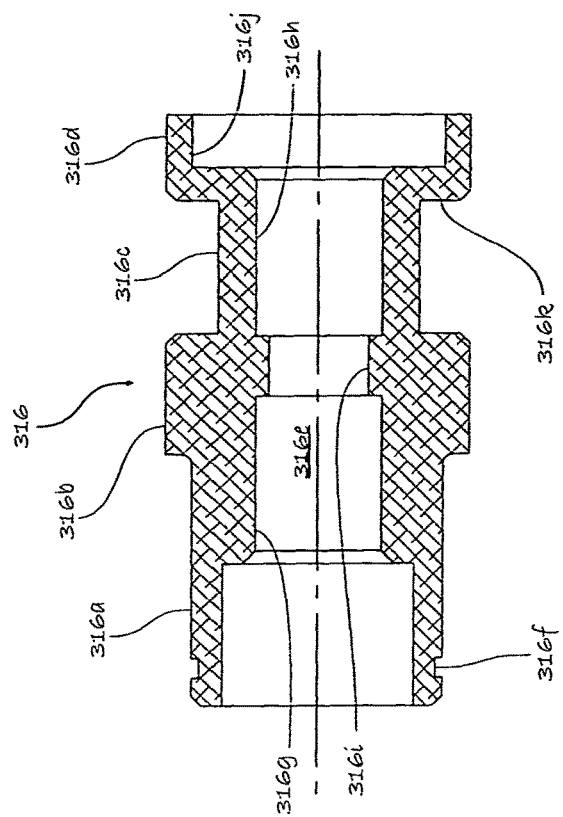
Figure 18:
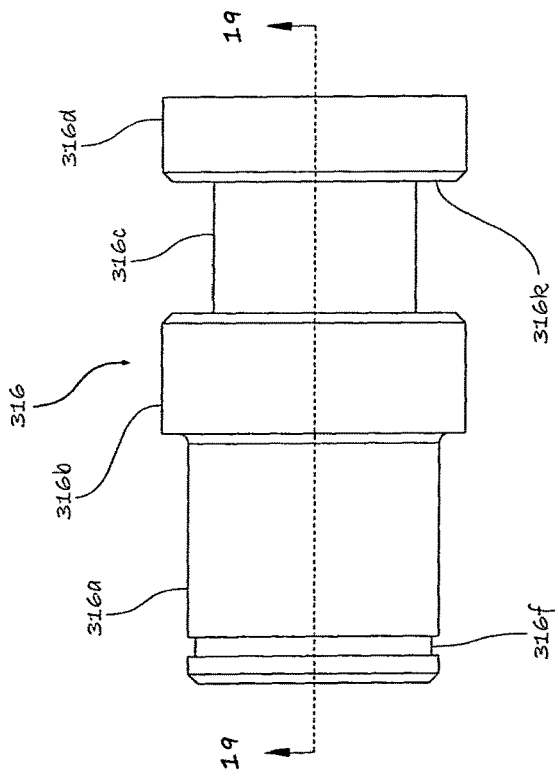
FIG. 18 is an elevation and FIG. 19 a cross-sectional view of a pivot axle, provided separately for clarity of the other views.

Thus, as shown in FIGS. 18 and 19, the outer surface of pivot axle 316 is formed to define a medial bearing surface 316a of a first diameter, having a snap-ring groove 316f therein, an intermediate bearing surface 316b of larger diameter than medial bearing surface 316a, a latching recess 316c of reduced diameter, an outer locating surface 316d defining a locking shoulder 316k, and a bore 316e. The inner surface of bore 316e is further formed to define bushing recesses 316g and 316h, pin bearing surface 316i, and an inner locating surface 316j.

Figure 16B:
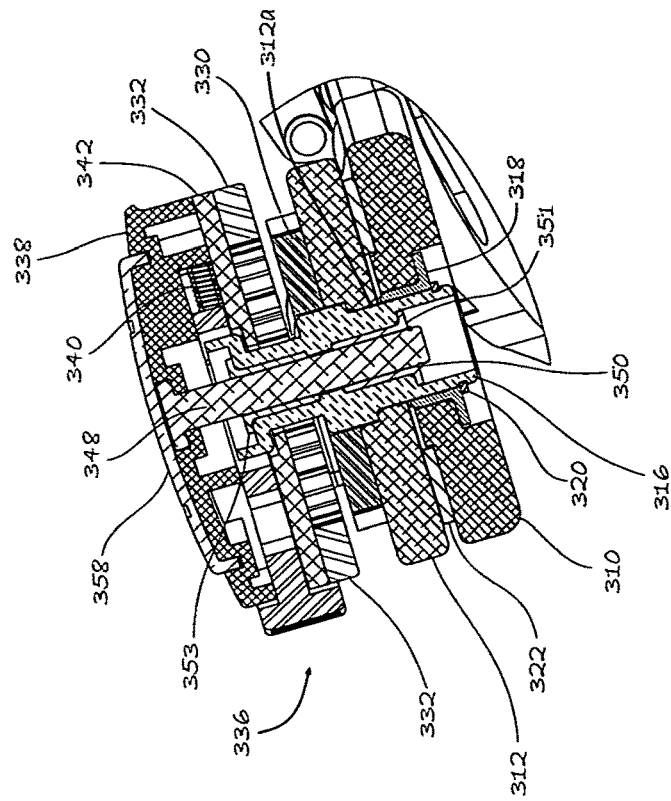
FIG. 16B is a comparable cross-sectional view taken along the line 16-16 of FIG. 15, with the sliding latch in the open position.
Figure 16A:
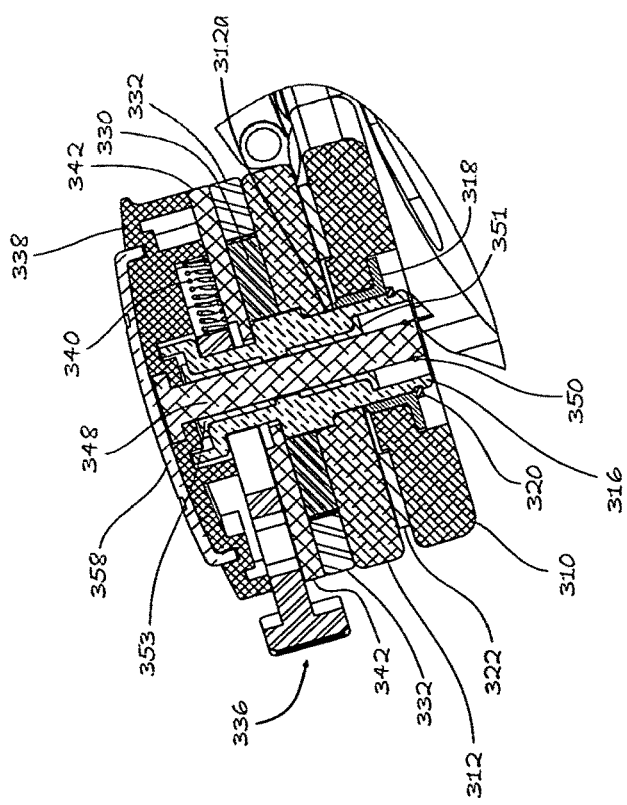
FIG. 16A is a cross-sectional view taken along the line 16-16 of FIG. 15, with the sliding latch in the closed position.
Figure 17B:
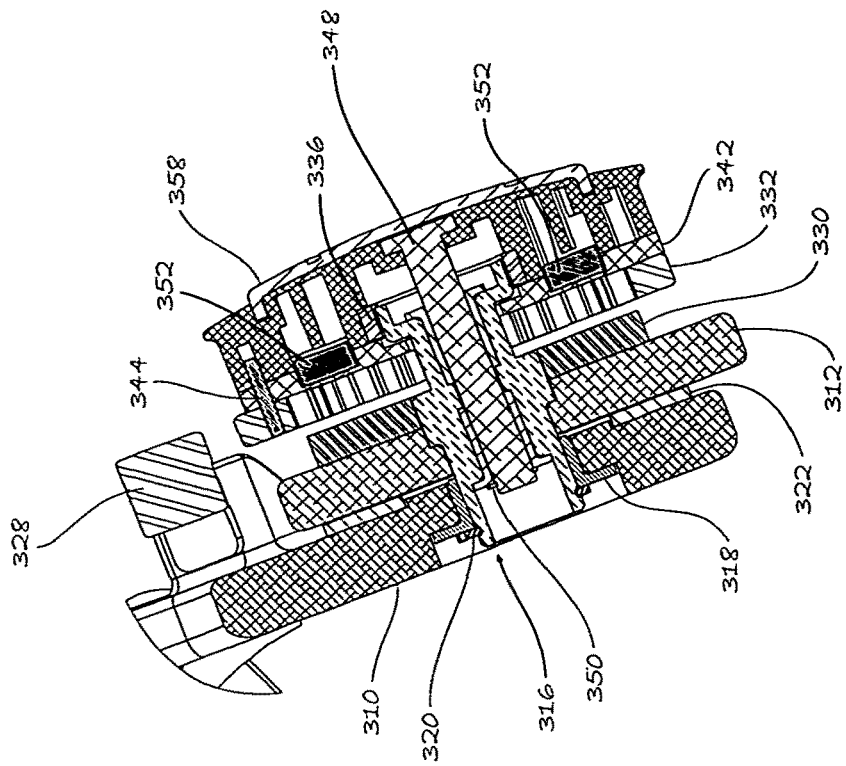
FIG. 17B is a similar cross-sectional view taken along the line 17-17 of FIG. 15, with the sliding latch in the open position.
Figure 17A:
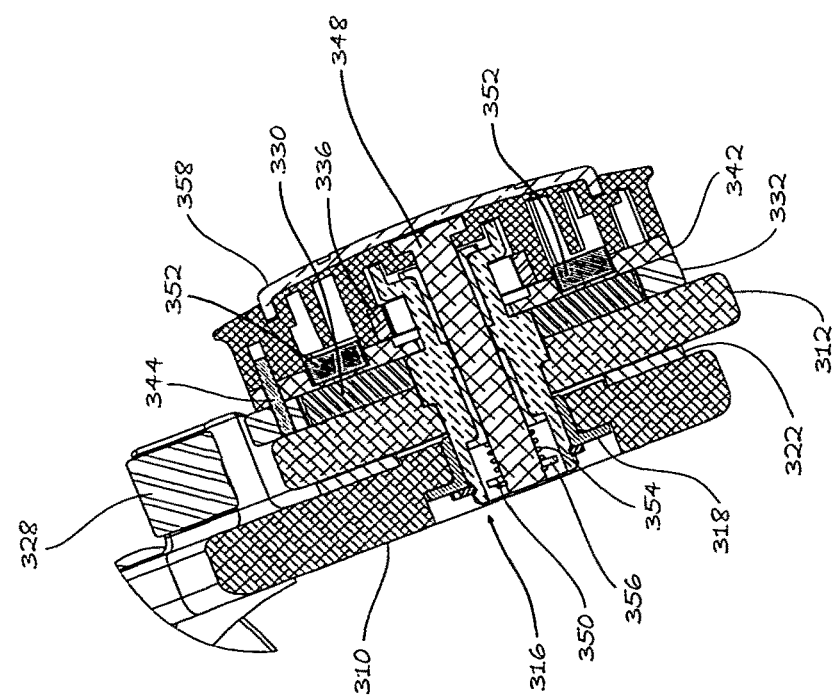
FIG. 17A is a cross-sectional view taken along the line 17-17 of FIG. 15, with the sliding latch in the closed position.

As shown in the cross-sectional views of FIGS. 16A and B and FIGS. 17A and B, the lower side plate 312 is formed to define a stepped bore 312a, so that when the pivot axle 316 is inserted into bore 312a, lower side plate 312 is located by the intersection of the stepped bore 312a with the junction of medial bearing surface 316a and intermediate bearing surface 316b. This can be a press-fit, so that lower side plate 312 and pivot axle 316 rotate together with respect to upper side plate 310. Upper side plate 310 fits over the inner end of inner bearing surface 316a, with a bushing 318 interposed therebetween, to permit free rotation. The assembly of upper and lower side plates 310 and 312 and pivot axle 316 is made permanent by a snap-ring 320 fitting into snap-ring groove 316f.

If the upper and lower side plates 310 and 312 respectively are made of a material tending to gall, such as if they were machined or cast of aluminum, a thrust washer 322 made of a low-friction plastic material such as acetal may be interposed therebetween. Washer 322 can be retained in position by a spring pin 324 received in mating bores in washer 322 and upper side plate 310. If the upper and lower side plates 310 and 312 are made of a non-galling material, such as if molded of plastic, thrust washer 322 can be omitted.

The same pivot joint structure, with the pivot axle 316 cut off at the right side of the intermediate bearing surface 316b (referring to FIGS. 18 and 19) can be used on the medial side of joint brace 300 to join the medial upper and lower side plates 310 and 312.

In accordance with the objects of the invention, the range of motion (ROM) permitted by the joint brace 300 of the invention is to be readily adjustable to allow convenient variation of the ROM, for example as a patient recovers from injury or surgery.

Limitation of the ROM is provided by cooperating stop members secured to the upper and lower side plates 310 and 312 which abut to prevent further relative rotation, thus limiting the ROM. Adjustability of the ROM is provided by making one of the stop members movable with respect to the corresponding side plate. In the embodiment shown, a stop member 326 is fixed to upper side plate 310, while a stop member 328 is assembled to lower side plate 312 in a manner such that its orientation can be readily adjusted to allow selection of a desired ROM. However, the relative disposition of these functions could be reversed, and this is to be considered to be within the scope of the invention.

As illustrated, upper stop member 326 may comprise a pad 326*a* of a hard rubber or like resilient material, to absorb the shock of the stop members coming into contact with one another.

To provide relative angular adjustment of the positions of stop members 326 and 328, cooperating gears 330 and 332 are provided. Gear 330 has external teeth and gear 332 internal teeth 332*a*, of the same specification, so that when the teeth of the gears 330 and 332 are engaged, relative motion thereof is prevented. Gear 330 is fixed to lower side plate 312 by pins 334, while gear 332 is formed integrally with or fixedly assembled to stop member 328. Thus, when gear 332 is intermeshed with gear 330, and the lower cuff 306 is rotated together with lower side plate 312 as the fetlock is extended—that is, upon clockwise rotation of the lower cuff 306 in the view of FIG. 6, for example—the ROM of the joint is limited when stop member 328 abuts stop member 326.

As above, ready and convenient adjustment of the ROM permitted, without tools and without the possibility of losing parts, is an object of the invention. Adjustment is provided in the following way: gear 332 is simply moved axially outwardly out of engagement with gear 330, the assembly of gear 332 and stop member 328 rotated to the desired position, and gear 332 resecured in engagement with gear 330.

The mechanism whereby gear 332 can be conveniently released from engagement with gear 330 and resecured thereto after adjustment as desired is accordingly an important aspect of the invention. This is accomplished as follows.

The principal mechanism for releasably securing the gears 332 and 330 in engagement with one another comprises a sliding latch 336. As shown most clearly in FIG. 11, sliding latch defines a generally racetrack-shaped aperture—essentially having two semi-circular ends separated by straight sections—indicated at 336*a* and closed by a lower engaging member 336*b*. Sliding latch 336 slides in a passageway 338*c* defined by opposed parallel walls 338*a* formed in a molded slider assembly cap 338, and is biased outwardly by a spring 340 received in a recess 338*b* in a slider assembly cap 338. A contoured outer contact surface 336*c* is provided to receive a user's finger, to press sliding latch 336 inwardly against the bias of spring 340. Sliding latch 336 is confined in passageway 338*c*, and spring 340 in recess 338*b*, by a slider assembly plate 342. Gear 332 and slider assembly plate 342 are secured to slider assembly cap 338 by pins 344, forming a unitary ROM stop assembly 346 in which the only moving parts are sliding latch 336 and spring 340. An outer decorative cap 358 completes the ROM stop assembly 346.

As shown by the cross-sectional views of FIGS. 16A and B, and FIGS. 17A and B, the ROM stop assembly 346 is assembled to the assembly of pivot axle 316 and upper and lower side plates 310 and 312 by a headed pin 348 received in a central bore in slider assembly cap 338, and having a circlip groove 348*a* at its medial end. Pin 348 may be secured to slider assembly cap 338 when the latter is molded. Groove 348*a* passes through the bore in axle 316 and receives a circlip 350 to secure the ROM stop assembly 346 to the assembly of upper and lower side plates 310 and 312. Medial and lateral bushings 351 and 353 respectively are preferably provided between pin 348 and pivot axle 316. Pin 348 fits slidingly within central pin bearing surface 316*i* of axle 316.

As also shown by the cross-sectional views of FIGS. 16A and B, and FIGS. 17A and B, pivot axle 316 fits within aperture 336*a* of sliding latch 336. As can be seen by comparison of FIGS. 16A and B, in the locked position of FIG. 16A, the lower engaging member 336*b* of latch 336 fits within latching recess 316*c* of axle 316, bearing against locking shoulder 316*k*, and held in this "locked" position by spring 340, thus securing the ROM stop assembly 346 such that gears 330 and 332 are intermeshed, preventing relative rotation thereof and thereby fixing the position of stop member 328. Accordingly, in order to adjust the ROM permitted, the sliding latch is pushed in by one's finger, against the bias of spring 340, disengaging lower engaging member 336*b* of latch 336 from latching recess 316*c* of axle 316, to take an "unlocked" position, as shown by FIG. 16B. The ROM stop assembly 346 can then be pulled axially outwardly, disengaging gears 330 and 332 from one another, to the position shown in FIGS. 16B and 17B, rotated to the position desired, and moved in the medial direction, back to the locked position. The distance through which ROM stop assembly 346 can thus be pulled axially outwardly is controlled by the spacing between circlip 350 and the medial end surface of medial bushing 351. When the ROM stop assembly 346 again reaches its original locked position as shown in FIGS. 16A and 17A, spring 340 urges sliding latch 336 outwardly, such that lower engaging member 336*b* of latch 336 again engages latching recess 316*c* of axle 316, securing ROM stop assembly 346 in the locked position.

It will be apparent that it would be possible, albeit unlikely, for a clod of dirt, a stone or a stick to be thrown up during exercise of a horse fitted with the joint brace of the invention in such a way as to depress sliding latch 336 and allow rotation of gear 332 with respect to gear 330, thus varying the ROM permitted and possibly leading to injury. To prevent this, a second restraining mechanism is provided that keeps ROM stop 346 in the locked position even after sliding latch 336 is moved inwardly, that is, such that some amount of force must be exerted to move ROM stop assembly 346 axially outwardly after latch 336 is disengaged from axle 316.

In the preferred embodiment shown, this additional restraining mechanism is provided by magnets 352, which are retained in cooperating recesses 342*a* in slider assembly plate 342 and 338*d* in slider assembly cap 338. Magnets 352 are closely juxtaposed to gear 330 when the ROM stop assembly 346 is in the engaged position of FIGS. 16A and 17A, and exert an attractive force on gear 330, so that this force must be overcome by force exerted by one's hand pulling outwardly on the ROM stop assembly 346 in order to move gear 332 out of engagement with gear 330 and adjust the ROM permitted. An additional restraint is thus provided.

This magnetic restraint requires that gear 330 at least comprise some quantity of, or be made entirely of, a ferromagnetic material, possibly ferromagnetic stainless steel. A different way of providing an additional restraining mechanism would be to provide a spring 354 under a washer 356 and secured by the circlip at the medial end of pin 348. See FIG. 17A. This would likewise require axial outward force to be exerted in order to disengage gear 332 from gear 330 and would provide an additional restraint. This alternative would also allow elimination of magnets 352, would allow gear 330 to be made of a less expensive and lighter-weight material, e.g., to be molded of plastic, and would allow slider assembly plate 352 to be thinner, since it would not need to define recesses 342*a* for receiving magnets 352. On the other hand, one advantage of use of magnets as opposed to a spring is that the force exerted by the magnets is reduced as the gear 332 is withdrawn, making it easier for the user to hold the ROM stop assembly 346 in the unlocked position; if a spring is used, the force required to hold the ROM stop assembly 346 in the unlocked position is increased as the ROM stop assembly 346 is withdrawn.

Again, the choice of materials for gears 330 and 332 will depend on the use. In an equine application, these gears will likely need to be made of metal; in a human application, they may be molded of plastic.

It will also be appreciated that the number of intermeshing teeth on gears 330 and 332 will control the number of choices of ROM made available; if a 5° adjustment is desired, 72 teeth will be needed on gears 330 and 332.

The latch could also be provided in different form. For example, a lever pivoted about an axis perpendicular to the axis of the axle 316 and off-center to one side of the slider assembly cap 338 could be employed to releasably secure gears 330 and 332 in engagement with one another.

Finally, as mentioned earlier one goal of the invention is to provide indicia indicating the amount of ROM permitted, so as to allow convenient setting of the ROM by engagement of gears 330 and 332 at a desired relative position. This is accomplished as shown by Detail A in FIG. 8, and in FIGS. 11 and 12. A series 360 of numerals indicating varying amounts of degrees of ROM are stamped or engraved on the outer circumference of the gear 332, opposite a fiducial mark 362 on the lower arm 312. As the gear 332 is rotated to set the ROM, a different one of the series 360 of numerals is disposed opposite fiducial mark 362, indicating the degree of ROM permitted.

Figure 3:
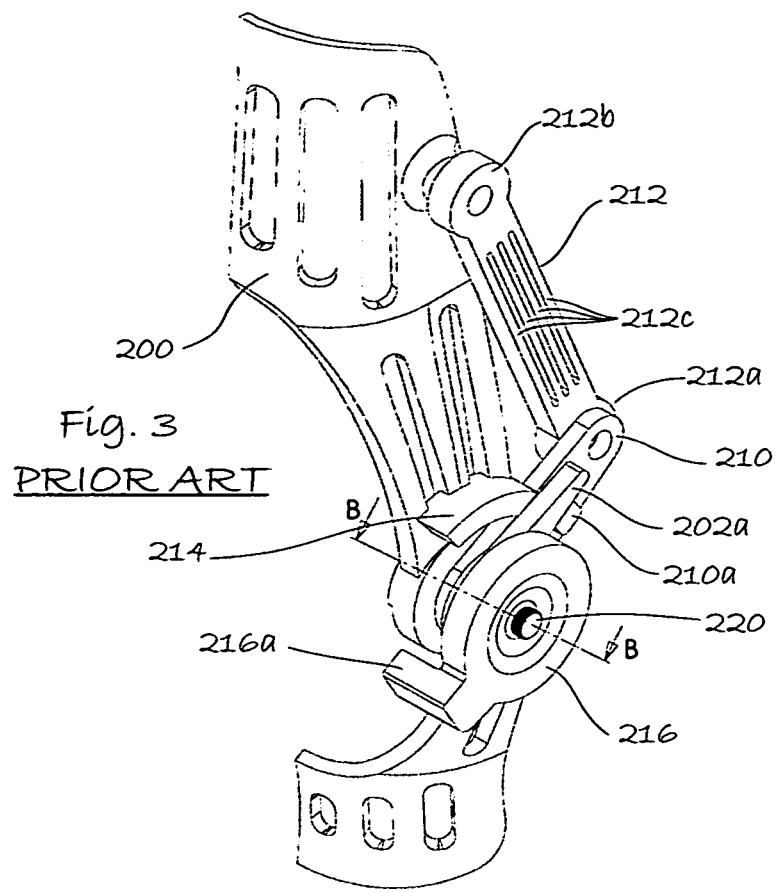
FIG. 3, corresponding to FIG. 35 of Ser. No. 14/106,300, shows an enlarged view similar to FIG. 1, with the device assembled.
Figure 4:
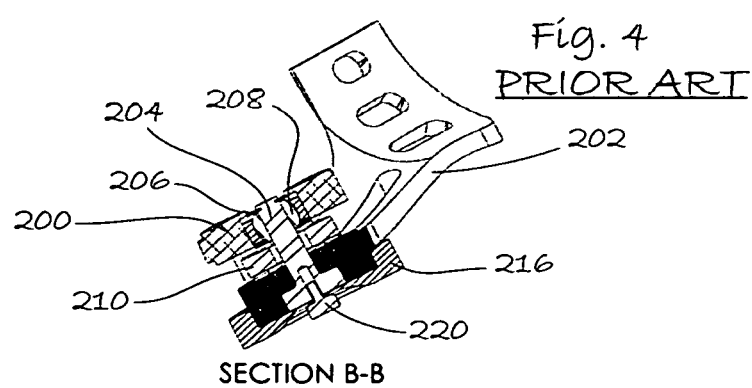
FIG. 4, corresponding to FIG. 36 of Ser. No. 14/106,300, is a cross-sectional view taken along the line B-B of FIG. 3.

As mentioned above, the ROM stop of the invention could also be employed in a joint brace also providing resilient members assisting in supporting the joint, as in FIGS. 1-3.

Therefore, while a preferred embodiment of the invention has been disclosed in detail, the invention is not limited thereto, but only by the following claims.

What is claimed is:

1. A joint support device for limiting a range of motion of a joint disposed between proximal and distal sections of a limb, said joint defining an axis of rotation, said joint support device comprising:
a proximal cuff, adapted to fit closely about said proximal section of said limb, and be secured thereto;
a distal cuff, adapted to fit closely about said distal section of said limb, and be secured thereto;
said proximal and distal cuffs each being secured to respective proximal and distal side plates on both medial and lateral sides thereof, said proximal and distal side plates comprising cooperating bores for receiving medial and lateral pivot axles, such that said proximal and distal side plates can be assembled to one another, thereby defining an axis of rotation of said joint support device substantially aligned with the axis of rotation of said joint;
a first stop member fixed to one of said proximal and distal side plates on at least one of said medial and lateral sides, and a second stop member releasably secured to the other of said proximal and distal side plates on the same one of said medial and lateral sides, said first and second stop members being located so as to contact one another upon extension of said joint, so as to limit the range of motion of the joint;
wherein the second stop member releasably secured to the other of said proximal and distal side plates can be released therefrom, rotated in order to adjust the range of motion of the joint to be permitted, and resecured thereto; and
wherein said second stop member is releasably secured to the other of said proximal and distal side plates by a first mechanism that requires a user to apply force against a bias provided by a biasing member to release the second stop member from the other of said proximal and distal side plates, and by a second mechanism operable by the user without tools to release the second stop member from the other of said proximal and distal side plates.

2. The joint support device of claim 1, wherein the first stop member is fixed to the proximal side plate and the second stop member is releasably secured to the distal side plate.

3. The joint support device of claim 1, comprising a first gear fixed to the other of said proximal and distal side plates and a second gear to which said second stop member is fixed, said first and second gears being intermeshed with one another to secure said second stop member with respect to the other of said proximal and distal side plates, and wherein said first and second mechanisms are operated by a user to remove said second gear from said first gear in order to adjust the range of motion of the joint to be permitted.

4. The joint support device of claim 3, wherein said first gear is generally circular and has teeth on its outer periphery and said second gear is of ring form and has intermeshing teeth on an inner surface of said ring, such that when said second gear is secured around said first gear, said second stop member is fixed with respect to the other of said proximal and distal side plates, and such that said second gear can be withdrawn axially from around said first gear to adjust the range of motion of said device.

5. The joint support device of claim 4, wherein said first mechanism operable by a user to release and resecure the second stop member from the other of said proximal and distal side plates comprises a latch that must be operated by a user against the bias of said biasing member in order to allow said second gear to be withdrawn axially from around said first gear to adjust the range of motion of said device.

6. The joint support device of claim 5 wherein said latch comprises a sliding latch pushed radially inwardly against the bias of said biasing member in order to allow said second gear to be withdrawn axially from around said first gear to adjust the range of motion of said device.

7. The joint support device of claim 6, wherein said sliding latch is secured axially with respect to said second gear, and comprises a generally racetrack-shaped aperture therein, fitting over a pivot axle having a locking recess terminated by a shoulder, whereby said sliding latch bears against said shoulder to secure the second gear around the first gear, and whereby when said sliding latch is pushed radially inwardly, a distal portion of said latch is moved past said shoulder, allowing said sliding latch and the second stop member to be moved axially outwardly.

8. The joint support device of claim 7, wherein said sliding latch is confined in a passageway defined between a slider assembly cap and a slider assembly plate.

9. The joint support device of claim 1, wherein said second mechanism that that is operable without tools to remove the second stop member from the other of said proximal and distal side plates comprises magnets that exert an attractive force urging said second gear into engagement with said first gear.

10. The joint support device of claim 1, wherein said second mechanism that that is operable without tools to remove the second stop member from the other of said proximal and distal side plates comprises a further spring biasing said second gear into engagement with said first gear.

11. The joint support device of claim 1, wherein said biasing member is a spring.

12. A joint support device for limiting a range of motion of a joint disposed between proximal and distal sections of a limb, said joint defining an axis of rotation, said joint support device comprising:
- a proximal cuff, adapted to fit closely about said proximal section of said limb, and be secured thereto;
- a distal cuff, adapted to fit closely about said distal section of said limb, and be secured thereto;
- said proximal and distal cuffs each being secured to respective proximal and distal side plates on both medial and lateral sides thereof, said proximal and distal side plates comprising cooperating bores for receiving medial and lateral pivot axles, such that said proximal and distal side plates can be assembled to one another, thereby defining an axis of rotation of said joint support device substantially aligned with the axis of rotation of said joint;
- a first stop member fixed to one of said proximal and distal side plates on at least one of said medial and lateral sides, and a second stop member releasably secured to the other of said proximal and distal side plates on the same one of said medial and lateral sides, said first and second stop members being located so as to contact one another upon extension of said joint, so as to limit the range of motion of the joint;
- wherein the second stop member releasably secured to the other of said proximal and distal side plates can be released therefrom, rotated in order to adjust the range of motion of the joint to be permitted, and resecured thereto; and
- wherein said second stop member is releasably secured to the other of said proximal and distal side plates by a mechanism operable by a user without tools to release the second stop member from the other of said proximal and distal side plates,
- a first gear fixed to the other of said proximal and distal side plates and a second gear, fitting around said first gear, and to which said second stop member is fixed, said first and second gears being intermeshed with one another to secure said second stop member with respect to the other of said proximal and distal side plates, and wherein said mechanism is operated by a user to remove said second gear from around said first gear in order to adjust the range of motion of the joint to be permitted,
- said mechanism comprising a latch that must be operated by a user against the bias of a biasing member in order to allow said second gear to be withdrawn axially from around said first gear to adjust the range of motion of said device.

13. The joint support device of claim 12 wherein the first stop member is fixed to the proximal side plate and the second stop member is releasably secured to the distal side plate.

14. The joint support device of claim 12, wherein said first gear is generally circular and has teeth on its outer periphery and said second gear is of ring form and has intermeshing teeth on an inner surface of said ring, such that when said second gear is secured around said first gear, said second stop member is fixed with respect to the other of said proximal and distal side plates, and such that said second gear can be withdrawn axially from around said first gear to adjust the range of motion of said device.

15. The joint support device of claim 12 wherein said latch comprises a sliding latch pushed radially inwardly against the bias of said biasing member in order to allow said second gear to be withdrawn axially from around said first gear to adjust the range of motion of said device.

16. The joint support device of claim 15, wherein said sliding latch is secured axially with respect to said second gear, and comprises a generally racetrack-shaped aperture therein, fitting over a pivot axle having a locking recess terminated by a shoulder, whereby said sliding latch bears against said shoulder to secure the second gear around the first gear, and whereby when said sliding latch is pushed radially inwardly, a distal portion of said latch is moved past said shoulder, allowing said sliding latch and the second stop member to be moved axially outwardly.

17. The joint support device of claim 16, wherein said sliding latch is confined in a passageway defined between a slider assembly cap and a slider assembly plate.

18. The joint support device of claim 12, further comprising a second mechanism that requires the user to apply force to remove the second stop member from the other of said proximal and distal side plates comprises magnets that exert an attractive force urging said second gear into engagement with said first gear.

19. The joint support device of claim 12, further comprising a second mechanism that requires the user to apply force to remove the second stop member from the other of said proximal and distal side plates, said second mechanism comprising a biasing member biasing said second gear into engagement with said first gear.

20. The joint support device of claim 12, wherein said biasing member is a spring.

* * * * *